United States Patent [19]

Kameswaran

[11] Patent Number: 5,449,789
[45] Date of Patent: Sep. 12, 1995

[54] DEBROMINATIVE CHLORINATION OF PYRROLES

[75] Inventor: Venkataraman Kameswaran, Princeton Junction, N.J.

[73] Assignee: American Cyanamid Company, Wayne, N.J.

[21] Appl. No.: 983,204

[22] Filed: Nov. 30, 1992

[51] Int. Cl.$^6$ .................... C07B 39/00; C07D 207/34
[52] U.S. Cl. .................................... 548/561; 548/531; 548/532; 548/537; 548/543; 548/557; 548/558
[58] Field of Search ............... 548/531, 532, 537, 543, 548/557, 558, 561

[56] References Cited

U.S. PATENT DOCUMENTS

| | | | |
|---|---|---|---|
| 4,647,576 | 3/1987 | Hoefle | 514/22 |
| 5,008,403 | 4/1991 | Kameswaran | 548/561 |
| 5,010,098 | 4/1991 | Brown et al. | 514/426 |
| 5,157,047 | 10/1992 | Kameswaran | 514/427 |
| 5,162,308 | 11/1992 | Brown et al. | 514/63 |

FOREIGN PATENT DOCUMENTS 0372263  6/1990  European Pat. Off. .

*Primary Examiner*—Mark L. Berch
*Attorney, Agent, or Firm*—Gregory M. Hill

[57] ABSTRACT

There is provided a simple quantitative procedure for the chlorination of pyrrole compounds containing electron withdrawing substituents via the displacement of bromine with chlorine on the pyrrole nucleus.

7 Claims, No Drawings

DEBROMINATIVE CHLORINATION OF PYRROLES

BACKGROUND OF THE INVENTION

A wide variety of pyrrole compounds substituted with one to three chlorine atoms on the pyrrole ring are highly useful as fungicidal, insecticidal, molluscicidal, acaricidal and nematocidal agents. However, chlorination of these pyrrole compounds frequently proves to be difficult due to over chlorination and/or oxidation of the pyrrole ring.

It is an object of this invention to provide a simple quantitative procedure for introducing chlorine substituent(s) to pyrrole compounds containing electron withdrawing groups. It is another object of this invention to provide a convenient and readily available source of chlorinated pesticidal pyrrole compounds.

SUMMARY OF THE INVENTION

This invention relates to a process for the preparation of a chlorinated pyrrole compound comprising reacting a pyrrole compound containing at least one electron withdrawing substituent and at least one hydrogen or bromine substituent with a chlorinating agent in the presence of a solvent, and when the pyrrole compound containing at least one electron withdrawing substituent has no bromine substituents on the pyrrole ring, in the presence of a catalytic amount of bromine. In particular, this invention relates to a process for the preparation of a chlorinated pyrrole compound of formula I

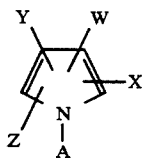
(I)

wherein W is CN, $NO_2$, $CO_2R_1$, $CONR_2R_3$, $CSNR_4R_5$ or $S(O)_nCF_2R_6$;

X is Cl or phenyl optionally substituted with one to three $C_1$-$C_4$alkyl, $C_1$-$C_4$alkoxy, $C_1$-$C_4$alkylthio, $C_1C_4$alkylsulfinyl, $C_1$-$C_4$alkysulfonyl, F, Cl, Br, I, CN, $NO_2$, $CF_3$, $R_7CF_2B$, $R_8CO$ or $NR_9R_{10}$ groups;

Y is $CF_3$, Cl or phenyl optionally substituted with one to three $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, F, Cl, Br, I, CN, $NO_2$, $CF_3$, $R_7CF_2B$, $R_8CO$ or $NR_9R_{10}$ groups;

Z is Cl or $CF_3$ with the proviso that at least one of X, Y or Z must be Cl;

A is hydrogen or $C_1$-$C_6$alkyl;

$R_1$ is $C_1$-$C_6$alkyl, $C_3$-$C_6$cycloalkyl or phenyl;

$R_2$, $R_3$, $R_4$ and $R_5$ are each independently hydrogen, $C_1$-$C_4$alkyl, $C_1$-$C_4$haloalkyl or phenyl optionally substituted with one or more Cl, Br, I, F, $NO_2$, CN, $C_1$-$C_4$alkyl, $C_1$-$C_4$haloalkyl, $C_l$-$C_4$alkoxy or $C_1$-$C_4$haloalkoxy groups;

$R_6$ is hydrogen, F, Cl, Br, $CF_2H$, $CCl_2H$, $CF_3$ or $CCl_3$;

$R_7$ is hydrogen, F, $CHF_2$, CHFCl or $CF_3$;

$R_8$ is hydrogen or $C_1$-$C_4$alkyl;

$R_9$ is hydrogen or $C_1$-$C_4$alkyl;

$R_{10}$ is hydrogen, $C_1$-$C_4$alkyl or $R_{11}CO$;

$R_{11}$ is hydrogen or $C_1$-$C_4$alkyl;

B is $S(O)_m$ or oxygen; and m and n are each independently an integer of 0, 1 or 2;

which comprises reacting a compound of formula II

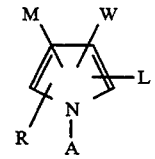
(II)

wherein L is hydrogen, Br or phenyl optionally substituted with one to three $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, F, Cl, Br, I, CN, $NO_2$, $CF_3$, $R_7CF_2B$, $R_8CO$ or $NR_9R_{10}$ groups;

M is hydrogen, Br, $CF_3$ or phenyl optionally substituted with one to three $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, F, Cl, Br, I, CN, $NO_2$, $CF_3$, $R_7CF_2B$, $R_8CO$ or $NR_9R_{10}$ groups;

R is hydrogen, Br or $CF_3$ with the proviso that at least one of L, M or R must be hydrogen or Br; and W, A, $R_7$, $R_8$, $R_9$ and $R_{10}$ are as described above for formula I;

with a chlorinating agent in the presence of a solvent and, when L, M and R are other than Br, in the presence of a catalytic amount of bromine.

Pyrrole compounds of formula I are useful as insecticides, molluscicides, acaricides, nematocides and fungicides.

DETAILED DESCRIPTION OF THE INVENTION

The present invention provides a simple procedure for the introduction of chlorine to a pyrrole ring via the displacement of the appropriate bromopyrrole precursor. Direct chlorination of the pyrrole ring via the displacement of hydrogen is frequently difficult. Such reactions often result in low yields of the desired product and the generation of undesirable side-products due to over chlorination and ring oxidation. It has now been found that debrominative chlorination, the displacement of one or more bromine atoms on the pyrrole ring by chlorine, proceeds in a simple quantitative manner, thereby facilitating the chlorination of electron deficient pyrroles under mild reaction conditions to give the desired product in high purity and yield.

In particular, this invention relates to a process for the preparation of a chlorinated pyrrole compound of formula I

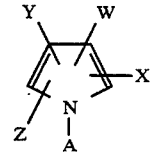
(I)

wherein W is CN, $NO_2$, $CO_2R_1$, $CONR_2R_3$, $CSNR_4R_5$ or $S(O)_nCF_2R_6$;

X is Cl or phenyl optionally substituted with one to three $C_1$-$C_4$alkyl, $C_1$-$C_4$alkoxy $C_1$-$C_4$alkylthio, $C_1$-$C_4$alkylsulfinyl, $C_1$-$C_4$alkylsulfonyl, F, Cl, Br, I, CN, $NO_2$, $CF_3$, $R_7CF_2B$, $R_8CO$ or $NR_9R_{10}$ groups;

Y is $CF_3$, Cl or phenyl optionally substituted with one to three $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, F, Cl, Br, I, CN, $NO_2$, $CF_3$, $R_7CF_2B$, $R_8CO$ or $NR_9R_{10}$ groups;

Z is Cl or $CF_3$ with the proviso that at least one of X, Y or Z must be Cl;

A is hydrogen or $C_1$-$C_6$alkyl;

$R_1$ is $C_1$-$C_6$alkyl, $C_3$-$C_6$cycloalkyl or phenyl;

$R_2$, $R_3$, $R_4$ and $R_5$ are each independently hydrogen, $C_1$-$C_4$alkyl, $C_1$-$C_4$haloalkyl or phenyl optionally substituted with one or more Cl, Br, I, F, $NO_2$, CN, $C_1$-$C_4$alkyl, $C_1$-$C_4$haloalkyl, $C_1$-$C_4$alkoxy or $C_1$-$C_4$haloalkoxy groups;

$R_6$ is hydrogen, F, Cl, Br, $CF_2H$, $CCl_2H$, $CF_3$ or $CCl_3$;

$R_7$ is hydrogen, F, $CHF_2$, CHFCl or $CF_3$;

$R_8$ is hydrogen or $C_1$-$C_4$alkyl;

$R_9$ is hydrogen or $C_1$-$C_4$alkyl;

$R_{10}$ is hydrogen, $C_1$-$C_4$alkyl or $R_{11}CO$;

$R_{11}$ is hydrogen or $C_1$-$C_4$alkyl;

B is $S(O)_m$ or oxygen; and m and n are each independently an integer of 0, 1 or 2;

which comprises reacting a compound of formula II

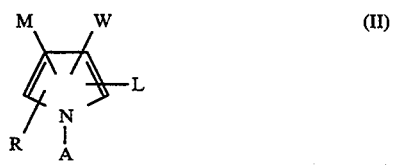
(II)

wherein L is hydrogen, Br or phenyl optionally substituted with one to three $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, F, Cl, Br, I, CN, $NO_2$, $CF_3$, $R_7CF_2B$, $R_8CO$ or $NR_9R_{10}$ groups;

M is hydrogen, Br, $CF_3$ or phenyl optionally substituted with one to three $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, F, Cl, Br, I, CN, $NO_2$, $CF_3$, $R_7CF_2B$, $R_8CO$ or $NR_9R_{10}$ groups;

R is hydrogen, Br or $CF_3$ with the proviso that at least one of L, M or R must be hydrogen or Br; and W, A, $R_7$, $R_8$, $R_9$ and $R_{10}$ are as described above for formula I;

with a chlorinating agent in the presence of a solvent and, when L, M and R are other than Br, in the presence of a catalytic amount of bromine.

According to the method of the invention, the appropriate bromopyrrole precursor may be formed in situ by chlorinating a pyrrole compound with no bromine substituents on the pyrrole ring in the presence of a catalytic amount of bromine. Typically, the catalytic amount of bromine ranges between about 0.01 and 1 mole %, e.g., about 0.1 mole %, depending on the specific reaction conditions. An example is shown in flow diagram I, wherein A and W are as described hereinabove.

Flow Diagram I

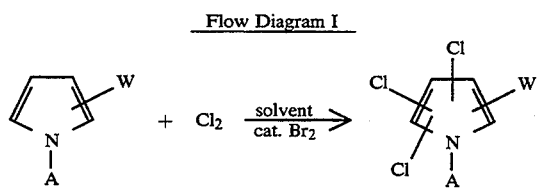

Alternatively, the method of the invention may be used to prepare the desired chloropyrrole product by the chlorination of the already formed and isolated bromopyrrole precursor. An example is shown in flow diagram II.

Flow Diagram II

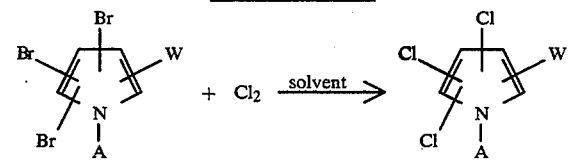

Compounds of formula II, which are useful as reactants in the method of the invention, and methods for their preparation, including typically useful reagents, are described in U.S. Pat. Nos. 5,010,098, 5,008,403 and 5,162,308 among other publications.

In general, the catalytic usage of bromine is more suitable for those pyrrole compounds of formula II wherein A is hydrogen and L, M and R are other than bromine. Otherwise, direct chlorination may take place when the pyrrole compound contains at least one hydrogen or bromine substituent.

Chlorinating agents known in the art such as chlorine gas, N-chlorosuccinimide, sulfuryl chloride, t-butylhypochlorite and the like are suitable for use in the method of invention.

Solvents which are unreactive toward chlorinating agents may be used in the method of invention, preferably those which are known to be suitable for chlorination reactions such as carbon tetrachloride, acetic acid, and haloaromatics such as chlorobenzene and the like.

The simple, quantitative method disclosed herein of introducing chlorine atoms to a pyrrole ring containing electron withdrawing substituent(s) may take place under mild reaction conditions such as room temperature. However, the reaction rate is proportional to the reaction temperature and, therefore, increased reaction temperatures give increased reaction rates and decreased reaction times. Sharp increases in reaction temperature, however, may lead to a decrease in desired product yield due to undesirable side-reactions and decomposition.

Flow diagrams I and II above provide illustrations of typical pyrrole compounds of formula I which may be prepared according to the method of the invention. In order to facilitate a further understanding of the invention, the following examples are presented to illustrate more specific details thereof. The invention is not to be limited thereby, except as defined in the appended claims.

EXAMPLE 1

Preparation of 4-Chloro-2-(p-chlorophenyl)-5-(trifluoromethyl)pyrrole-3-carbonitrile

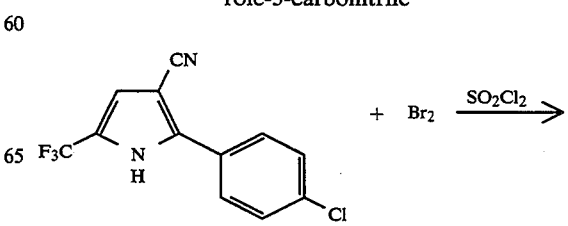

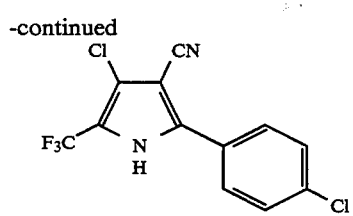

A mixture of 2-(p-chlorophenyl)-5-(trifluoromethyl)-pyrrole-3-carbonitile (8.12 g, 0.03 mol) and sodium acetate (0.25 g, 0.003 mol) in acetic acid at 70° C. is treated dropwise with bromine (0.48 g, 0.003 mol). When the color has disappeared, the reaction mixture is treated dropwise with sulfuryl chloride (6.1 g, 0.045 mol) over a 1 hour period, held at 70° C. for 1 hour, concentrated in vacuo and diluted with water. The reaction mixture is filtered, the filter cake is washed with water and dried to yield the title product as a white solid, 7.7 g (84% yield), mp 242°–243° C.

EXAMPLE 2

Preparation of 4-Chloro-2-(3,4-dichlorophenyl)-5-(trifluoromethyl)-pyrrole-3-carbonitrile

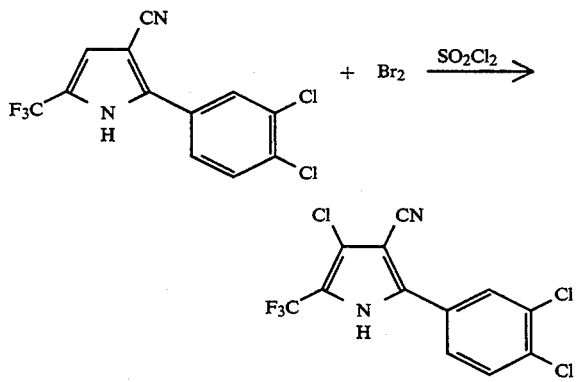

Using essentially the same procedure described in Example 1 and substituting 2-(3,4-dichlorophenyl)-5-(trifluoromethyl)pyrrole-3-carbonitrile as the starting material, the title product is obtained in 69% yield as a white solid, mp 239°–241° C.

EXAMPLE 3

Preparation of 4-Bromo-2-(p-chlorophenyl)-1-methyl-5-(trifluoromethyl)pyrrole-3-carbonitrile

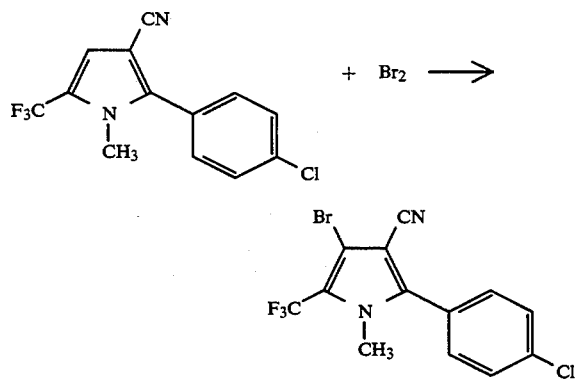

A solution of 2-(p-chlorophenyl)-1-methyl-5-(trifluoromethyl)pyrrole-3-carbonitrile (5.0 g, 0.0176 mol) in carbon tetrachloride is treated with bromine (56 g, 0.0351 mol), heated at reflux temperature for 8 hours, cooled, washed sequentially with water, aqueous sodium metabisulfite and water, dried over sodium sulfate and concentrated in vacuo to give a solid residue. The residue is recrystallized from heptane to give the title product as a white solid, 6.0 g (94% yield), mp 126°–129° C.

EXAMPLE 4

Preparation of 4-Chloro-2-(p-chlorophenyl)-1-methyl-5-(trifluoromethyl)pyrrole-3-carbonitrile

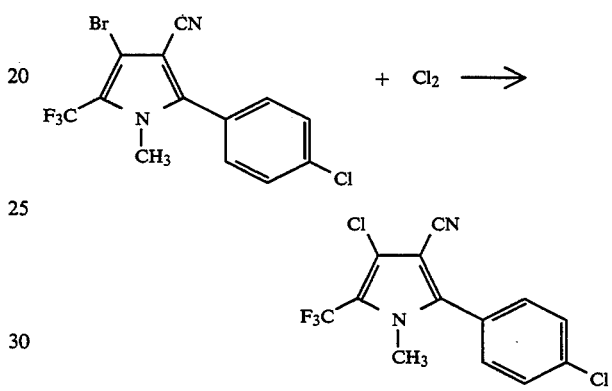

A solution of 4-bromo-2-(p-chlorophenyl)-1-methyl-5-(trifluoromethyl)pyrrole-3-carbonitrile (20.0 g, 0.055 mol) in chlorobenzene at 60° C. is treated with chlorine gas at 60° C. over a ½ hour period, cooled to room temperature, washed sequentially with water, aqueous sodium metabisulfite and water, dried over sodium sulfate and concentrated in vacuo to give a residue. The residue is crystallized in heptane to give the title product as a pale yellow solid, 17.6 g (quantitative yield), mp 109.5°–110.5° C.

EXAMPLE 5

Preparation of 1-Methyl-2,4,5-trichloropyrrole-3-carbonitrile

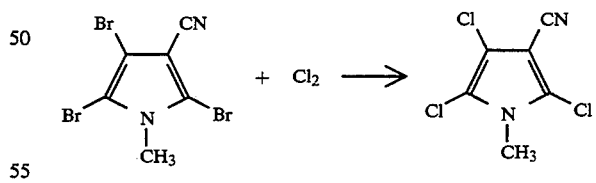

A mixture of 1-methyl-2,4,5-tribromopyrrole-3-carbonitrile (40.0 g, 0.117 mol) in chlorobenzene is heated to 40° C., treated with chlorine gas at a rate sufficient to maintain a reaction temperature below 35° C. while using ice-bath cooling. When addition is complete, the reaction mixture is cooled to room temperature, washed sequentially with water, sodium metabisulfite and water, dried over sodium sulfate and concentrated in vacuo to give a residue. The residue is crystallized in heptane to give the title product as a white solid, 22.8 g (93% yield), mp 113°–114° C.

I claim:

1. A debrominative chlorination process for preparing a chlorinated pyrrole compound wherein said chlorinated pyrrole compound has structural formula I

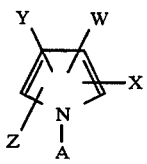

wherein W is CN, $NO_2$, $CO_2R_1$, $CONR_2R_3$, $CSNR_4R_5$ or $S(O)_nCF_2R_6$;

X is Cl or phenyl optionally substituted with one to three $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, F, Cl, Br, I, CN, $NO_2$, $CF_3$, $R_7CF_2B$, $R_8CO$ or $NR_9R_{10}$ groups;

Y is $CF_3$, Cl or phenyl optionally substituted with one to three $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, F, Cl, Br, I, CN, $NO_2$, $CF_3$, $R_7CF_2B$, $R_8CO$ or $NR_9RO_{10}$ groups;

Z is Cl or $CF_3$ with the proviso that at least one of X, Y or Z must be Cl;

A is hydrogen or $C_1$-$C_6$alkyl;

$R_1$ is $C_1$-$C_6$alkyl, $C_3$-$C_6$cycloalkyl or phenyl;

$R_2$, $R_3$, $R_4$ and $R_5$ are each independently hydrogen, $C_1$-$C_4$alkyl, $C_1$-$C_4$haloalkyl, or phenyl optionally substituted with one or more Cl, Br, I, F, $NO_2$, CN, $C_1$-$C_4$alkyl, $C_1$-$C_4$haloalkyl, $C_1$-$C_4$alkoxy or $C_1$-$C_4$haloalkoxy groups;

$R_6$ is hydrogen, F, Cl, Br, $CF_2H$, $CCl_2H$, $CF_3$ or $CCl_3$;

$R_7$ is hydrogen, F, $CHF_2$, CHFCl or $CF_3$;

$R_8$ is hydrogen or $C_1$-$C_4$alkyl;

$R_9$ is hydrogen or $C_1$-$C_4$alkyl;

$R_{10}$ is hydrogen, $C_1$-$C_4$alkyl or $R_{11}CO$;

$R_{11}$ is hydrogen or $C_1$-$C_4$alkyl;

B is $S(O)_m$ or oxygen; and m and n are each independently an integer of 0, 1 or 2;

which comprises reacting a compound of formula II

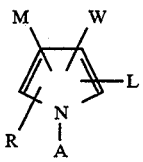

wherein L is hydrogen or phenyl optionally substituted with one to three $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, F, Cl, Br, I, CN, $NO_2$, $CF_3$, $R_7CF_2B$, $R_8CO$ or $NR_9R_{10}$ groups;

M is hydrogen, $CF_3$ or phenyl optionally substituted with one to three $C_1$-$C_4$alkyl, $C_1$-$C_4$alkoxy, $C_1$-$C_4$alkylthio, $C_1$-$C_4$ alkylsulfinyl, $C_1$-$C_4$alkylsulfonyl, F, Cl, Br, I, CN, $NO_2$, $CF_3$, $R_7CF_2B$, $R_8CO$ or $NR_9R_{10}$ groups;

R is hydrogen or $CF_3$ with the proviso that at least one of L, M or R must be hydrogen; and W, A, $R_7$, $R_8$, $R_9$ and $R_{10}$ are as described above;

with an effective amount of a chlorinating agent other than t-butyl hypochlorite in the presence of a solvent and in the presence of a catalytic amount of bromine, to produce the compound of formula I.

2. The process according to claim 1 for the preparation of a compound of formula I wherein W is CN, X is Cl or Br, Y is Cl or phenyl optionally substituted with one to three Cl, Br, I or $CF_3$ groups and Z is $CF_3$ or Cl.

3. The process according to claim 1 wherein A is hydrogen.

4. The process according to claim 1 wherein the solvent is chlorobenzene.

5. The process according to claim 1 wherein A is methyl.

6. The process according to claim 4 wherein A is hydrogen.

7. The process according to claim 1 wherein the chlorinating agent is selected from the group consisting of chlorine gas, sulfuryl chloride and N-chlorosuccinimide.

* * * * *